United States Patent [19]

Sorenson et al.

[11] 4,167,190
[45] Sep. 11, 1979

[54] PULSE DOSAGE CONTROL UNIT FOR TISSUE STIMULATION SYSTEM

[75] Inventors: Paul D. Sorenson, Blaine; Larry A. McNichols, Coon Rapids, both of Minn.

[73] Assignee: Medtronic, Inc., Minneapolis, Minn.

[21] Appl. No.: 844,178

[22] Filed: Oct. 21, 1977

[51] Int. Cl.² ............................................. A61N 1/36
[52] U.S. Cl. ................................................ 128/423 R
[58] Field of Search ..................... 128/421, 422, 423 R

[56] References Cited
U.S. PATENT DOCUMENTS 3,888,261  6/1975  Maurer ............................... 128/421
3,983,881  10/1976  Wickham .......................... 128/422

FOREIGN PATENT DOCUMENTS

2242996  4/1975  France ..................................... 128/422

Primary Examiner—William E. Kamm
Attorney, Agent, or Firm—R. Lewis Gable; Karl A. Baumgardner

[57] ABSTRACT

A method and apparatus for applying electrical stimulation to areas of the nervous system wherein the method permits precise pulse dosage control over prescribed time intervals to be exercised by the administering physician, and the apparatus is organized to provide the desired pulse dosage by means of selectable duty cycle on/off modulation of a pulse train having selectable pulse repetition rates and pulse widths. Digital circuitry is used in a pulse counting technique to implement the generation of pulse sequences such that direct quantitative control may be exercised.

18 Claims, 3 Drawing Figures

PULSE DOSAGE CONTROL UNIT FOR TISSUE STIMULATION SYSTEM

BACKGROUND OF THE INVENTION

1. Field of the Invention

The present invention relates generally to the field of neutral pulse stimulation system and more particularly to control circuits directed to providing quantitative control of such systems.

More specifically, this invention relates to methods and apparatus for controlling the quantity of energy delivered to body tissue in a given time by accurately controlling the pulse dosage by means of digital control circuitry.

2. Description of the Prior Art

Devices and techniques for applying electrical pulse stimulation to various parts of the human body are, of course, well known. Over the recent past, these devices and techniques have been progressively refined, and specialized apparatus for various pulse stimulation procedures have appeared. As an illustrative example of a system directed specifically to stimulation of an area or areas of the nervous system such as the cerebellum, reference is made to a Dual Channel Cerebellar System (Physican's Information Manual © published in 1976 by Medtronic, Inc.) which shows the use of a dual-channel apparatus having a two radio frequency capability for transmission of various stimulus pulses alternately to selected receptor sites such as the left anterior cerebellar cortex and the right anterior cerebellar cortex. Conventionally, the pulses are applied in a bipolar manner to alleviate deleterious effects which occur from unidirectional net current flows and are applied in alternate time intervals to minimize the fatigue of biochemical mechanisms such as depletion of neurotransmitter substances as synapic junctions. Additionally, very low power drain systems have evolved making it feasible to consider the implantation of counterpart receiving systems such that the stimulation procedure can be accomplished on successive occasions without unduly traumatizing the patient with repetitive electrode positioning.

An example of an implantable system for stimulation of body tissue is provided in U.S. Pat. No. 3,773,051 to Wade G. Holcomb et al. Holcomb teaches the use of an RF link to deliver pulses of prescribed amplitudes to body tissue wherein a single channel transmitter is used to transmit pulses of controlled durations to an implanted receiver which converts the transmitteed duration information into amplitude information prior to applying the stimulation in the form of pulses to the electrode site. The technique disclosed is particularly effective in assuring the transmission of controllable amplitude pulses despite the vagaries of the radio frequency (illustratively 300 Khz-3Mhz—i.e., MF to HF range) propagation path.

U.S. Pat. No. 3,888,261 to Donald D. Mauer, and assigned to the same assignee of the present application, teaches the techniques of using a pair of transmission channels to transmit pulse trains in a time-shared sequence to alternate receptor sites. The two-channel technique disclosed is well suited for carrying independent stimulus pulse trains to the separate sites and is exploited by having each time-shared channel adapted to carry pulse trains of independently controllable amplitude. Also of interest in Maurer is the use of a pair of distinct frequencies in the RF link such that the independent pulse trains generated are assured of being unambiguously carried in isolated channels to their intended receptor site.

While the available devices and techniques represent useful solutions to a number of difficulties associated with administering pulse stimulation to highly sensitive portions of human body tissue, none have addressed a key aspect of pulse stimulation—that of administering precise pulse dosages. The present invention is directed to providing a useful solution of this specific problem area.

SUMMARY OF THE INVENTION

It is a primary object of this invention to provide improved apparatus for exercising quantitative control of the administration of stimulus pulses to areas of nerve tissue.

A further object of the present inventors is to control the number of stimulus pulses, or a dose, to be administered while having the capability of controlling also the pulse energy applied to nerve tissue, by means of a pulse counting duty cycle imposing circuit.

Another object of the present invention is to provide a pulse dosage control circuit which employs digital counting techniques to implement the pulse quantification processing.

Another object of the present invention is to provide apparatus for administering stimulus pulses wherein the precise energy content of a pulse dose is exercised to minimize the fatigue of biochemical mechanisms, such as the depletion of neurotransmitter substances at synapic junctions.

Another object of the present invention is to provide apparatus for administering stimulus pulses wherein the precise energy content of a pulse dose is exercised to minimize the chances of tissue damage during the administration of the prescribed doses.

In accordance with these and other objects of this invention, there is provided an apparatus for controlling the energy content of a dose of electrical pulses, comprising a generator for providing a first train of pulses, a divider circuit for dividing the first train of pulses to provide a second continuous train of pulses having a given period between pulses, and a duty cycle control circuit for producing first and second initiate signals and a terminate signal. The terminate signal occurs a first interval after the first initiate signal of at least one pulse period, while the second initiate signal occurs a second interval after the terminate signal of a selected whole number of the pulse periods. Further there is included a gate responsive to the first and second initiate signals and to the terminate signal for facilitating the passage of the first train of pulses for the first interval and for preventing the passage of the first train of pulses for the second interval, whereby the dosage of the electrical pulses to the body tissue is controlled.

BRIEF DESCRIPTION OF THE DRAWINGS

Additional objects and advantages of the invention will become apparent to those skilled in the art as the description proceeds with reference to the accompanying drawings wherein.

DETAILED DESCRIPTION OF THE PREFERRED EMBODIMENT

Figure 1:
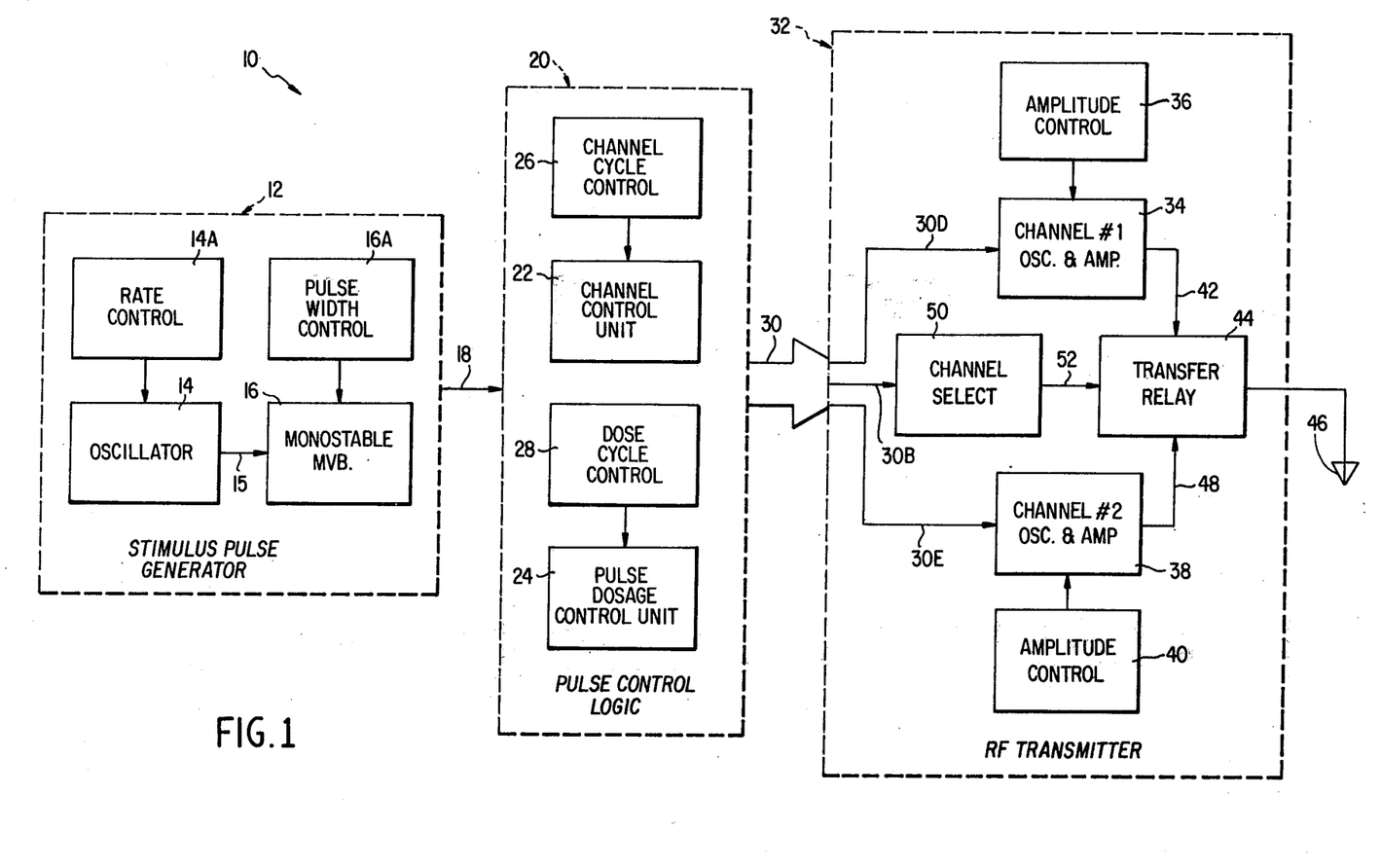
FIG. 1 is a block diagram of a neural stimulation system embodying the circuitry of the present invention.

Referring now to FIG. 1, there is shown a block diagram of a multi-channel body tissue stimulation system containing the pulse dosage control unit according to the present invention. The overall system 10 is comprised of a stimulus pulse generator 12, having a repetition rate oscillator 14 whose output is routed via a line 15 to a monostable multivibrator 16. The frequency of the oscillator 14 is controllable in discrete steps by means of a rate control 14A, and the pulse width of the monostable multivibrator 16 is controllable in discrete steps by means of a pulse width control 16A. The output of the stimulus pulse generator 12 is applied via a line 18 to a pulse control logic 20. The pulse control logic 20 is comprised of a channel control unit 22 and a pulse dosage control unit 24, and has a pair of input controls designated a channel cycle control 26 and a dose cycle control 28. The outputs of the pulse control logic 20 are directed via a group of lines 30 to a dual channel RF transmitter 32. The RF transmitter 32 has a first channel oscillator and amplifier unit 34 operable on a first frequency and controlled by an amplitude control 36, and a second channel oscillator and amplifier unit 38, operable on a second frequency and controlled by an amplitude control 40. A pair of lines 30D and 30E route pulse signals from the pulse control logic 20 to the first channel unit 34 and the second channel unit 38, respectively. The output of the first channel unit 34 is routed via a line 42 to a transfer relay 44 and thereafter to an antenna 46. The output of the second channel unit 38 is also applied to the transfer relay 44, via a line 48. A channel select unit 50 is controlled by signals in the pulse control logic 20, as supplied via a line 30B, and actuates the transfer relay 44 via a line 52.

An overview of the operation of the tissue stimulation system 10 is facilitated with continued reference to FIG. 1. Briefly, the stimulus pulse generator 12 provides a continuous train of stimulus pulses which are generated at a number of predetermined pulse rates controlled by the administering physician via the rate control 14A, and which have a number of predetermined pulse widths, controlled by the physician via the pulse width control 16A. The resulting first continuous pulse train, of preselected frequency and pulse width, is processed by the pulse control logic 20 so as to interrupt the first pulse train in accordance with a number of predetermined duty cycles, controlled by the physician via the dose cycle control 28. The pulse control logic 20 further alternating groups of the interrupted pulses (hereinafter pulse sequences) to the two output channels for transmission to and stimulation of the desired neural tissue. The RF transmitter 32, in concert with a cooperating receiver (not shown) which may be implanted in the body of the patient, serves to carry the two sequences of pulses to the tissue sites. Each channel of the RF transmitter 32 is keyed on by the presence of its respective pulse sequences, and is individually controllable in amplitude by means of the physician operated amplitude controls 36 and 40. The channel select unit 50 serves to alternately route the appropriate RF outputs from the two channels to the antenna 46 in response to control signals from the pulse control logic 20.

Functionally, the body tissue (e.g. neural) stimulation system 10 is used generally to apply bipolar electrical stimulation pulses to various tissue sites in the human boddy, a well known procedure in the healing arts. Common practice in the application of stimulus pulses calls for applying bipolar (area balanced) pulses to minimize potentially harmful effects due to a net unidirectional current flow, and further for introducing an on/off interval into the pulse streams to minimize the fatigue of biochemical mechanisms. In addition to these conventional features, the pulse dosage control unit 24 provides the capability for precisely controlling the number of stimulus pulses applied to the receiving site over a predetermined time interval by imposing a duty cycle pattern of the stimulus pulses. By selecting any of a wide range of duty cycles (in concert with selection of pulse rates, pulse-widths and channel alternation intervals) the physician may accurately and repeatably control the number of pulses, or alternately the pulse dosage, applied. As used herein, the term "dose" refers to the number of pulses that is applied to body tissue. In effect then, a pulse count rather than a prescribed on/off time is implemented and the pulse count, or pulse dosage, may be applied over a range of predetermined time intervals.

The range of specific values for the various physician-controlled parameters of an illustrative embodiment are as follows. The repetition rate oscillator 14 selectably produces six discrete frequencies: 10, 30, 50, 100, 150 and 200 Hz. The monostable multivibrator 16 operates on the particular frequency generated to produce a train of pulses wherein each pulse has selectable durations of 0.5, 0.75 or 1.0 milliseconds. The channel control unit 22 alternates the output of the stimulus pulse generator 12 to the first or second channels of the RF transmitter 32 on schedules of: 1, 4 or 8 minutes. And the pulse dosage control unit 24 selectably imposes the duty cycles of: full; two-thirds; one-half; one-third; or one-fifth on the stimulus pulses generated.

Figure 2:
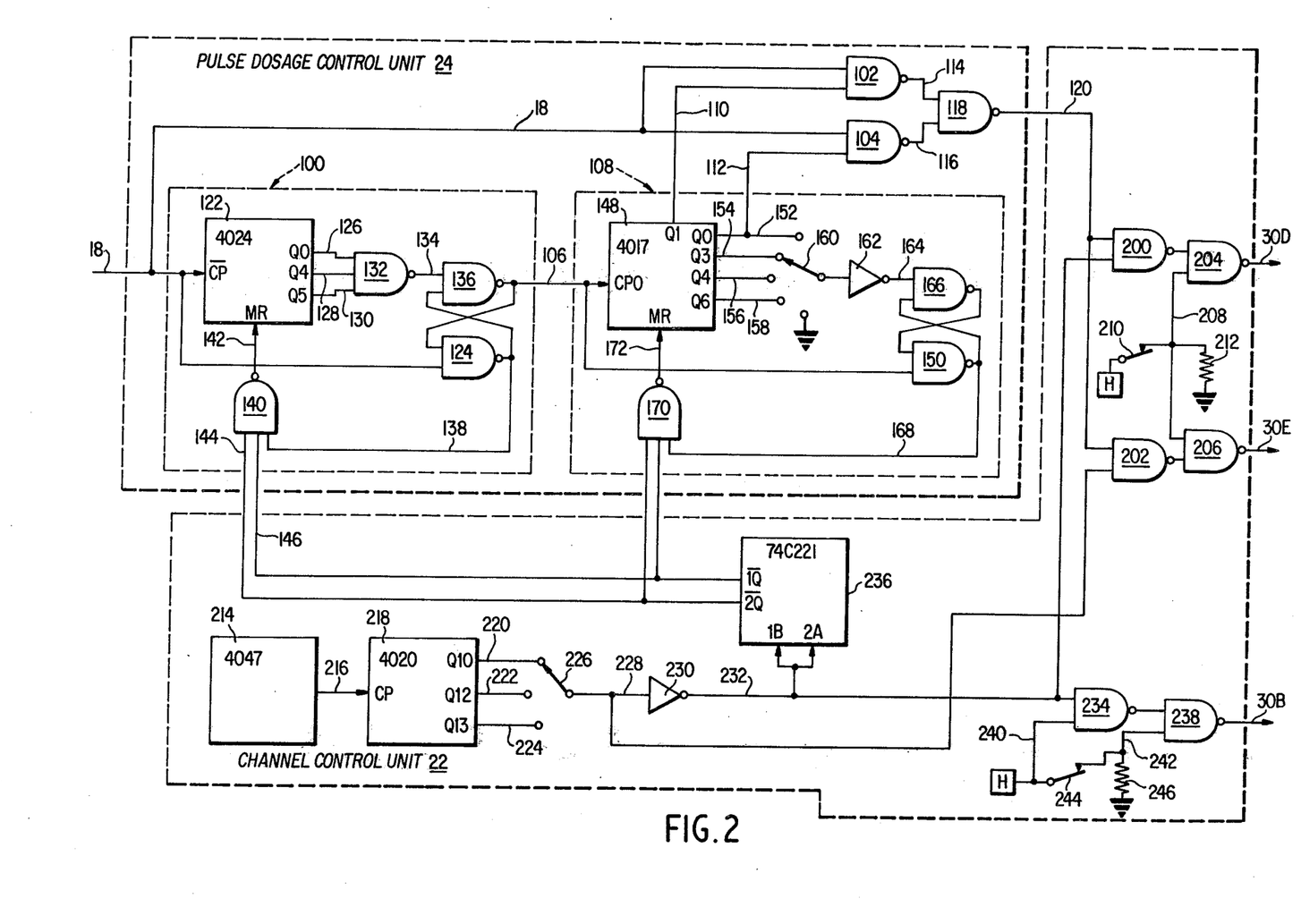
FIG. 2 is a logic diagram of a pulse control logic unit according to the present invention.

Referring now to FIG. 2, there is shown a detailed logic diagram of the pulse dosage control unit 24 and a simplified logic diagram of the channel control unit 22. Taken together the two units make up the pulse control logic 20 and, as shown in FIG. 1, they provide the quantitative pulse manipulations between the stimulus pulse generator 12 and the dual channel RF transmitter 32.

Stimulus pulses are inputted via the line 18 to a first input of a divide by 50 circuit 100, and to a first input of each of a pair of NAND gates 102 and 104. An output of the divide by 50 circuit 100 is routed via a line 106 to an input of a duty cycle circuit 108, whose output is provided via a pair of lines 110 and 112 to second inputs of NAND gates 102 and 104 respectively. Outputs of NAND gates 102 and 104 are routed via a pair of lines 114 and 116 respectively to two inputs of a NAND gate 118. An output of NAND gate 118 is routed via a line 120 to elements within the channel control unit 22.

Within the divide by 50 circuit 100, stimulus pulses are routed via the line 18 to a clock input CP of a 7-stage binary counter 122, and to a first input of a NAND gate 124. Three outputs of the 7-stage counter representing the $Q_0$, and $Q_4$ and $Q_5$ outputs are routed via lines 126, 128 and 130 respectively to three inputs of a NAND gate 132. The 7-stage counter may be of the type commercially available as CMOS type CD4024, or MC14024B, and the $Q_5$, $Q_4$ and $Q_0$ outputs conventionally represent pulse accumulations of 32, 16 and 1, respectively. An output of NAND gate 132 is routed via a line 134 to a first input of a NAND gate 136, whose output is presented on the line 106. NAND gates 124 and 136 are cross-coupled to implement the conventional R-S flip-flop. An output of NAND gate 124 is routed via a line 138 to a first input of a NAND gate 140, whose output is routed via a line 142 to a master reset MR input of the 7-stage counter 122. Two additional inputs are applied to the NAND gate 140 via lines 144 and 146, from sources external to the divide by 50 circuit 100 as described below. A detailed description of the divider circuit operation may be found in RCA COS/MOS Integrated Circuits Manual CMS-270 (1971) at page 77.

Functionally, the divide by 50 circuit 100 performs a conventional frequency division on the incoming stimulus pulses such that the output on line 106 provides a positive-going logic level transition for each 50 incoming pulses. This is accomplished regardless of which pulse rate or pulse width has been selected in the stimulus pulse generator 12.

Within the duty cycle circuit 108, the divided down stimulus pulses are inputted via the line 106 to a clock input CPO of a 5-stage Johnson decade counter 148, and to a first input of a NAND gate 150. The Johnson counter is well known in the art and may be of the type commercially available as CMOS type CD4017, or MC14017B. Four outputs of the Johnson counter 148 representing the $Q_0$, $Q_3$, $Q_4$ and $Q_6$ stages are routed via lines 152, 154, 156 and 158, respectively to four stationary contacts of a single-pole-five-throw switch, designated the dosage switch 160. The four stationary contacts represent the dosage switch 160 positions corresponding respectively to the FULL ($Q_0$/152) duty cycle; the $\frac{2}{3}$ ($Q_3$/154) duty cycle; the $\frac{1}{2}$ ($Q_4$/156) duty cycle; and the $\frac{1}{3}$ ($Q_6$/158) duty cycle. A fifth position of the dosage switch 160, which represents the 1/5 duty cycle position, is connected directly to the ground. A moveable contact of the dosage switch 160 is routed to both inputs of a NAND gate 162, whose output is routed via a line 164 to a first input of NAND gate 166. NAND gates 150 and 166 are cross-coupled to implement the conventional R-S flip-flop. An output of NAND gate 150 is routed via a line 168 to a first input of a NAND gate 170, whose output is routed via a line 172 to a master reset MR of the Johnson counter 148. Two additional inputs are applied to the NAND gate 170 via the lines 144 and 146, previously enumerated. The pair of lines 110 and 112 carry respectively the $Q_1$ and $Q_0$ outputs of the Johnson counter 148 to the NAND gates 102 and 104 as previously described.

Functionally, the duty cycle circuit 108, in combination with the three NAND gates 102, 104 and 118, serves to interrupt the continuous train of stimulus pulses inputted on the line 18 such that groups of 100 pulses (recall that a dose has been defined as a fixed number of pulses—illustratively 100) are clocked out and outputted on the line 120, and the groups (doses) are time-sequenced so as to implement the particular duty cycle called for by the setting of the dosage switch 160. On occurrence of a master reset, the $Q_0$ output of counter 148 will transition to a high logic level and the $Q_1$ through $Q_9$ outputs will all exhibit low logic levels. When the $Q_0$ output of the counter 148 transitions to a high logic level, there is provided a first initiate signal enabling the passage of stimulus pulses on input line 18 through the NAND gate 104. As the $Q_1$ output of the counter 148 is exhibiting a low logic level, the NAND gate 102 is disabled, hence its output on line 114 would be a high logic level which enables the NAND gate 118 to pass the stimulus pulses passed through the NAND gate 104 onto the line 120. This condition persists for an interval equal to 50 stimulus pulses. On occurrence of the first positive-going logic level transition on input line 106 (indicating the onset of the 51st stimulus pulse-after a master reset had occurred) the $Q_1$ output of counter 148 transitions to a high logic level and the $Q_0$ output transitions to a low logic level. Thus the roles of NAND gates 104 and 102 are reversed. The NAND gate 102, enabled by the high logic level on the line 110 carrying the $Q_1$ output, passes stimulus pulses and the NAND gate 104 is disabled. As before, the disabled gate enables the NAND gate 118 thereby permitting the passage of stimulus pulses onto the line 120. This condition also persists for an interval equal to 50 stimulus pulses. Overall, 100 pulses—a dose—are allowed to pass. On occurrence of a second positive-going logic level transition on input line 106, both the $Q_0$ and $Q_1$ outputs of the counter 148 transition to a low logic level, i.e., a terminate signal, thereby disabling NAND gates 102 and 104 and therefore inhibiting the passage of further stimulus pulses. When the next master reset signal is generated, a second initiate signal is generated in a manner as explained above.

Figure 3:
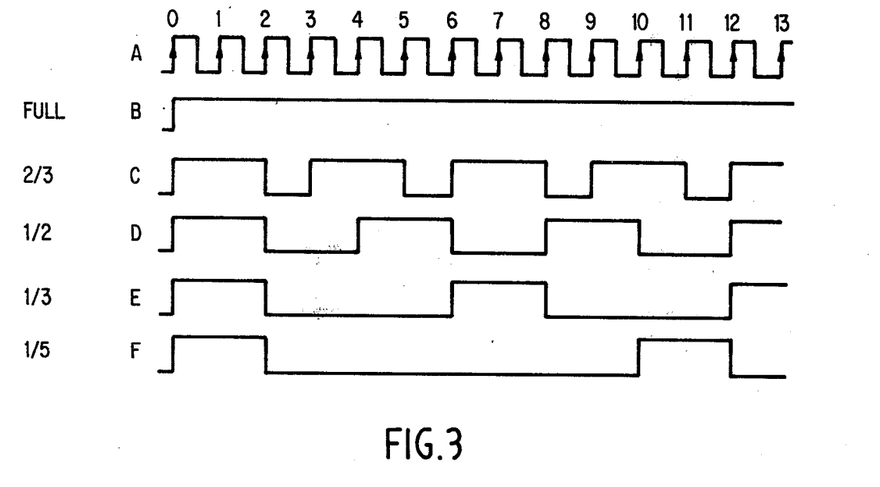
FIG. 3 depicts selected waveforms associated with the pulse dosage control unit.

For a description of how the dosage switch 160 effects the passage of further pulse doses, reference is made to the waveforms of FIG. 3 in addition to the circuitry of FIG. 2. Waveform A depicts the input pulses on line 106 resulting from dividing the stimulus pulses by 50. The upward arrows indicate the positive-going transitions to which the counter 148 responds, and the pulse numbers reflect the numerical sequence of positive-going transitions after a master reset. With the pulse dosage switch 160 in the $\frac{2}{3}$ position (as shown), the $Q_3$ output is routed to the NAND gate 162, and the C waveform reflects the envelope of the pulses present on the output line 120. As before, a master reset causes the $Q_0$ output to enable the passage of 50 pulses and a first positive-going transition on input line 106 causes the $Q_1$ output to enable the passage of an additional 50 pulses, via NAND gates 102 and 104. A second transition inhibits the passage of further pulses. On occurrence of a third positive-going transition on the input line 106, the $Q_3$ output of counter 148 transitions to a high logic level which toggles the R-S flip-flop (NAND gates 150 and 166) such that a low logic level is routed via the line 168 to NAND gate 170. The output of NAND gate 170 transitions to a high logic level which activates the master reset MR thereby restoring the counter 148 to the reset condition. The resetting action immediately clears the high logic level from the $Q_3$ output, and the $Q_0$ output again transitions to a high logic level. A cycle of operation, as described above, will then repeat itself. Therefore, the waveform C obtains, and the output line 120 will first carry 100 pulses (one dose), and will then carry no pulses for a 50 pulse interval, in repetitive fashion to implement the $\frac{2}{3}$ duty cycle mode. It should be noted that this action will occur for the full range of pulse rates and pulse widths outputted by the stimulus pulse generator 12.

For other positions of the dosage switch 160, similar duty cycles are implemented, as shown in FIG. 3. Briefly, in the $\frac{1}{2}$ position of dosage switch 160, the fourth positive-going transition on line 106 causes, as shown in the D waveform, the $Q_4$ output of counter 148 to transition to a high logic level, initiating a master reset. In the $\frac{1}{3}$ position of dosage switch 160, the $Q_6$ output of counter 148 initiates a master reset as before, as shown in the E waveform. In the 1/5 position of dosage switch 160, the counter 148 is self-resetting upon occurrence of the 10th positive-going transition on the line 106, as shown in the F waveform. Obviously, in the "full" position of the dosage switch 160, the counter 148 is reset for every positive-going transition (every 50 stimulus pulses) and therefore a continuous train of stimulus pulses occurs, as shown in the B waveform.

The two additional inputs on lines 144 and 146 to the NAND gates 140 and 170 play no intrinsic role in the operation of the pulse dosage control unit 24. The lines 144 and 146 carry negative pulses of short durations generated in the channel control unit 22 to coincide with channel alternation signals, as described below. On occurrence of these short negative pulses, both the divide by 50 circuit 100 and the duty cycle circuit 108 are simultaneously reset, thereby assuring synchronism between the processing of stimulus pulses in the pulse dosage control unit 22.

Within the channel control unit 22, the pulse sequences produced by the pulse dosage control unit 24 are inputted via the line 120 to first inputs of a pair of NAND gates 200 and 202. An output of NAND 200 is routed to a first input of NAND gate 204, whose output is presented on the line 30D. An output of NAND gate 202 is routed to a first input of NAND gate 206 whose output is presented on the line 30E. Second inputs of NAND gates 204 and 206 are tied together via a line 208 and are applied to a source of an enabling high logic level "H" through the normally closed contacts of a first test switch 210. A pull down resistor 212 is connected between the line 208 and logic ground.

A time base oscillator 214 applies its output via a line 216 to clock input of a 14-stage binary counter 218. The time base oscillator 214 may be a free-running astable multivibrator comprised of a CMOS type F4047, or CD4047A, integrated circuit having external R/C components (not shown) to precisely establish its operating frequency. The 14-stage binary counter 218 may be of the type commercially available as CMOS type F4020, or CD4020A. Three outputs of the 14-stage counter representing the Q10, Q12 and Q13 stages are routed via lines 220, 222 and 224 respectively to three stationary contacts of a single-pole-triple-throw switch, designated a channel alternation switch 226. The three stationary contacts represent the channel alternation switch 226 positions corresponding to the one minute interval (Q10/220); the four minute interval (Q12/222); and the eight minute interval Q13/224). A moveable contact of the channel alternation switch 226 is routed via a line 228 to an input of an inverting amplifier 230 and further to a second input of the NAND gate 202. The output of the inverting amplifier is applied via a line 232 to a second input of the NAND gate 200, to a first input of a NAND gate 234, and further to a pair of inputs of a monostable circuit 236. An output of NAND gate 234 is routed to a first input of a NAND gate 238, whose output is presented on the line 30B. A second input of NAND GATE 234 is directly connected to an enabling high logic level "H" via a line 240. A second input of NAND gate 238 is routed via a line 242 to the same high logic level source through the normally closed contacts of a second text switch 244. A pull down resistor 246 is connectedd between the line 240 and logic ground.

Functionally, the channel control unit 22 serves to route the pulse sequences from the pulse dosage control unit 24 to alternate channels of the dual channel RF transmitter 32 for a selectable time interval established by means of the channel alternation switch 226. Establishing the frequency of the time base oscillator 214 at 17.066 Hz and taking the Q10 output, representing the divide by 1024 stage, of the 14-stage counter 218 via the channel alternation switch 226 produces a voltage waveform on line 228 which remains at a high logic level for a period of 60 seconds (1/17.066)×1024, and at a low logic level for the same interval. During the time interval when line 228 is exhibiting a high logic level, the NAND gate 202 is enabled thereby passing the pulse sequences on the line 120 through the NAND gate 206 and the line 30E to the second channel of the RF transmitter 32 for application to the desired tissue receptor site. Also during this time interval, the output of the inverting amplifier 230 would be exhibiting a low logic level which would disable NAND gate 200 thereby rendering the first channel of the RF transmitter quiescent. During the time interval when the line 228 is exhibiting a low logic level, the roles of NAND gates 202 and 200 are reversed and the NAND gate 200 would be enabled thereby passing the pulse sequences on the line 120 through the NAND gate 204 and the line 30D to the first channel of the RF transmitter 32. Thus, for the one minute position of the channel alternation switch 226 (as shown) pulse sequences are routed alternately each minute to the first and second channels of the RF transmitter 32 via the lines 30D and 30E. This occurs similarly for the four minute position (1/17.066)×4096=240 seconds, corresponding to the Q12 stage of the 14-stage counter 218; and for the eight minute position (1/17.066)×8192=480 seconds corresponding to the Q13 stage of the 14-stage counter 218.

Whereas the NAND gates 200 and 202 serve to route stimulus pulses alternately to the two RF channels, the NAND gates 234 and 238 serve to provide the alternating control signals, via the line 30B, to the channel select unit 50 (shown in FIG. 1) to operate the transfer relay 44 thereby combining the outputs of the two RF channels onto a single antenna. The two test switches 210 and 244 serve to disable the output of the pulse dosage control unit 24 for secondary test purposes.

The monostable circuit 236 accepts the positive-going and negative-going transitions on the line 232 and produces negative-going pulses of short durations for each transition sensed. These short negative-going pulses are applied via the lines 144 and 146, as previously described, to assure synchronism between the pulse sequences produced in the pulse dosage control unit 24 and the channel alternation times produced in the channel control unit 22 by simultaneously resetting the divide by 50 circuit 100 and the duty cycle circuit 108.

Although the invention has been described in terms of a preferred embodiment, the invention should not be deemed limited thereto, since other embodiments and modifications will readily occur to one skilled in the art. It is therefore to be understood that the appended claims are intended to cover all such modifications and changes as fall within the true spirit and scope of the invention.

What is claimed is:

1. Apparatus for controlling the energy content and the number of pulses of a dose of electrical stimulation to be applied to by lead means coupled to nerve tissues, said apparatus comprising:
   (a) means for providing a continuous train of pulses at a selected frequency;

(b) duty cycle control means for producing first and second initiate signals and a terminate signal, said duty cycle means responsive to the occurrence of a predetermined number of pulses for providing said terminate signal occurring a first interval after said first initiate signal of at least one pulse period, said second initiate signal occurring a second interval after said terminate signal of a selected whole number of said pulse periods; and (c) gate means responsive to said first and second initiate signals and said terminate signal for facilitating the passage of said train of pulses between said first initiate and terminate signals and for preventing the passage of the train of pulses between said terminate and second initiate signals, whereby the dosage of the electrical pulses to the body tissue is constant regardless of the frequency selected.

2. Apparatus as claimed in claim 1, wherein said duty cycle control means comprises a counter responsive to said continuous train of pulses for providing at least first and second output signals each occurring at different numbers of occurrences of the pulses of said continuous train, and switch means for applying a selected one of said output signals to reset said counter means, whereby said second interval is variably controlled.

3. Apparatus as claimed in claim 2, wherein said gate means comprises first, second and third NAND gates, said continuous train of pulses being applied to a first input of said first and second NAND gates, said outputs of said first and second NAND gates being connected to the first and second inputs of said third NAND gate, first and second output signals of said counter being applied respectively to the second inputs of said first and second NAND gates to alternatively enable one of said first and second NAND gates to permit the passage of said continuous train of pulses via said one enabled NAND gate and said third NAND gate.

4. Apparatus as recited in claim 1, wherein there is included means for applying said pulse dosage to at least two different stimulation sites during alternate stimulation intervals wherein said pulse sequence is available for application to a first site only during a first stimulation interval and is available for application to a second site only during a second stimulation interval.

5. Apparatus as claimed in claim 4, wherein said applying means includes a first RF channel for providing an RF signal of a first type, a second RF channel for providing a second RF signal of a second type, and switch means coupled to receive the first and second RF signals for alternatively transmitting the first and second types of RF signals.

6. Apparatus as recited in claim 4, further comprising synchronizing means for synchronizing the onset of said pulse dosage with said alternate stimulation intervals.

7. Apparatus as recited in claim 4, wherein said switch means determines said first and second stimulation intervals to be substantially equal.

8. Apparatus as recited in claim 4, wherein said applying means comprises radio frequency transmission means for generating during said alternate stimulation intervals, different radio frequency carrier frequencies.

9. Apparatus as recited in claim 1, wherein said duty cycle control means sets said first interval to include two pulse periods and said second interval to a selectable number that takes on the values one, two, four and eight to implement pulse duty cycles of $\frac{2}{3}$, $\frac{1}{2}$, $\frac{1}{3}$ and 1/5 respectively.

10. Apparatus as recited in claim 9, wherein said generator means generates said continuous train of pulses at variable rates whereby a pulse dosage is made available for tissue stimulation in variable time intervals.

11. Apparatus as recited in claim 1, wherein said duty cycle control means sets said pulse period to be equal to a submultiple of a pulse dosage and said first interval to include two or more pulse periods.

12. Apparatus as claimed in claim 1, wherein said providing means includes generator means for providing a first train of pulses and divider means for dividing the first train of pulses to provide said continuous train of pulses having a given period between pulses.

13. Apparatus as recited in claim 12, wherein said generator means generates said first continuous train of pulses at variable rates whereby a pulse dose is made available for tissue stimulation in variable time intervals.

14. Apparatus as recited in claim 12, wherein said duty cycle control means sets said pulse period to be equal to a submultiple of a pulse dosage and said first interval to include two interpulse intervals and said pulse dose to include 100 pulses of said first train of pulses.

15. In a system for applying a dose of electrical signals to lead means coupled to tissue for the purposes of stimulating said tissue, pulse generator means comprising:

(a) means for generating a series of electrical signals having desired parameters adapted for being applied to said lead means; and (b) dose control means including counting means coupled to said generating means for counting the electrical signals to set independently of the desired parameters the number of a plurality of the electrical signals to define the dose, and means responsive to said counting means having counted the independently set number of the electrical signals for interrupting the application of said series of electric signals.

16. The invention according to claim 15;
wherein said pulse generator means further comprises output means adapted to being electrically coupled to said lead means;
wherein said dose control means includes gating means and gate control means, said gating means being coupled to said output means and having said series of electric signals applied thereto and further having a gate control signal applied thereto to control the passage therethrough of said series of electric signals to said output means, said gate control means being responsive to said counting means having counted the independently set number to provide said gate control signal to terminate the passage through said gating means of said series of electric signals.

17. The invention according to claim 16, wherein there is included means for setting said count set in said counting means.

18. Apparatus for controlling the energy content and the number of a plurality of pulses to define a dose of electrical stimulation to be applied via lead means coupled to nerve tissue, said apparatus comprising:

(a) means for providing a train of pulses of a variable, selected frequency; and (b) duty cycle control means coupled to said providing means to receive the train of pulses and including means for counting the regular pulses to set the number of a plurality of pulses within the dose independent of the selected frequency of the pulses to be applied to the nerve tissue during a first interval set by the number of pulses within the dose, and means responsive to said counting means having counted the set number of the plurality of pulses for terminating the application of the continuous train of pulses to the nerve tissue, and means for selectively choosing a second interval during which the application of the train of pulses to the nerve tissue is interrupted, whereby the duty cycle of the pulses in terms of the ratio of the first and second intervals and therefore the energy applied to the nerve tissue is controlled.

* * * * *

UNITED STATES PATENT AND TRADEMARK OFFICE
CERTIFICATE OF CORRECTION

PATENT NO. : 4,167,190

DATED : September 11, 1979

INVENTOR(S) : PAUL D. SORENSON, LARRY A. McNICHOLS

It is certified that error appears in the above—identified patent and that said Letters Patent are hereby corrected as shown below:

Col. 1, line 8, delete "neutral" and substitute therefore

--neural--.

Signed and Sealed this

Eighth Day of January 1980

[SEAL]

Attest:

SIDNEY A. DIAMOND

Attesting Officer     Commissioner of Patents and Trademarks